(12) United States Patent
Khorram

(10) Patent No.: US 6,477,853 B1
(45) Date of Patent: Nov. 12, 2002

(54) SYSTEM FOR PROLONGING USEFUL LIFE OF FOODSTUFFS IN A REFRIGERATOR

(76) Inventor: Ramin Khorram, 5 Tsienneto Rd.-#2, Derry, NH (US) 03038

( * ) Notice: Subject to any disclaimer, the term of this patent is extended or adjusted under 35 U.S.C. 154(b) by 0 days.

(21) Appl. No.: 09/801,431

(22) Filed: Mar. 7, 2001

(51) Int. Cl.$^7$ .......................... F25D 23/00; F25D 17/00
(52) U.S. Cl. ........................................ 62/264; 62/177
(58) Field of Search ............................. 62/78, 264, 177

(56) References Cited

U.S. PATENT DOCUMENTS 4,909,040 A * 3/1990 Feltrin ........................ 62/78
5,901,564 A * 5/1999 Comeau ...................... 62/264
5,918,773 A * 7/1999 Donovan et al. ........ 222/146.6
5,946,919 A * 9/1999 McKinney et al. ........... 62/3.7

\* cited by examiner

Primary Examiner—William C. Doerrler
(74) Attorney, Agent, or Firm—Mirick, O'Connell, DeMallie & Lougee, LLP

(57) ABSTRACT

A system for retarding food spoilage in a refrigerator, comprising an ultraviolet light mounted within the refrigerator, which is turned on for at least a predetermined time only after the refrigerator door is shut, to bathe foodstuffs in at least a portion of the refrigerator with UV light for a sufficient time to kill at least some of the organisms on the foodstuffs.

21 Claims, 1 Drawing Sheet

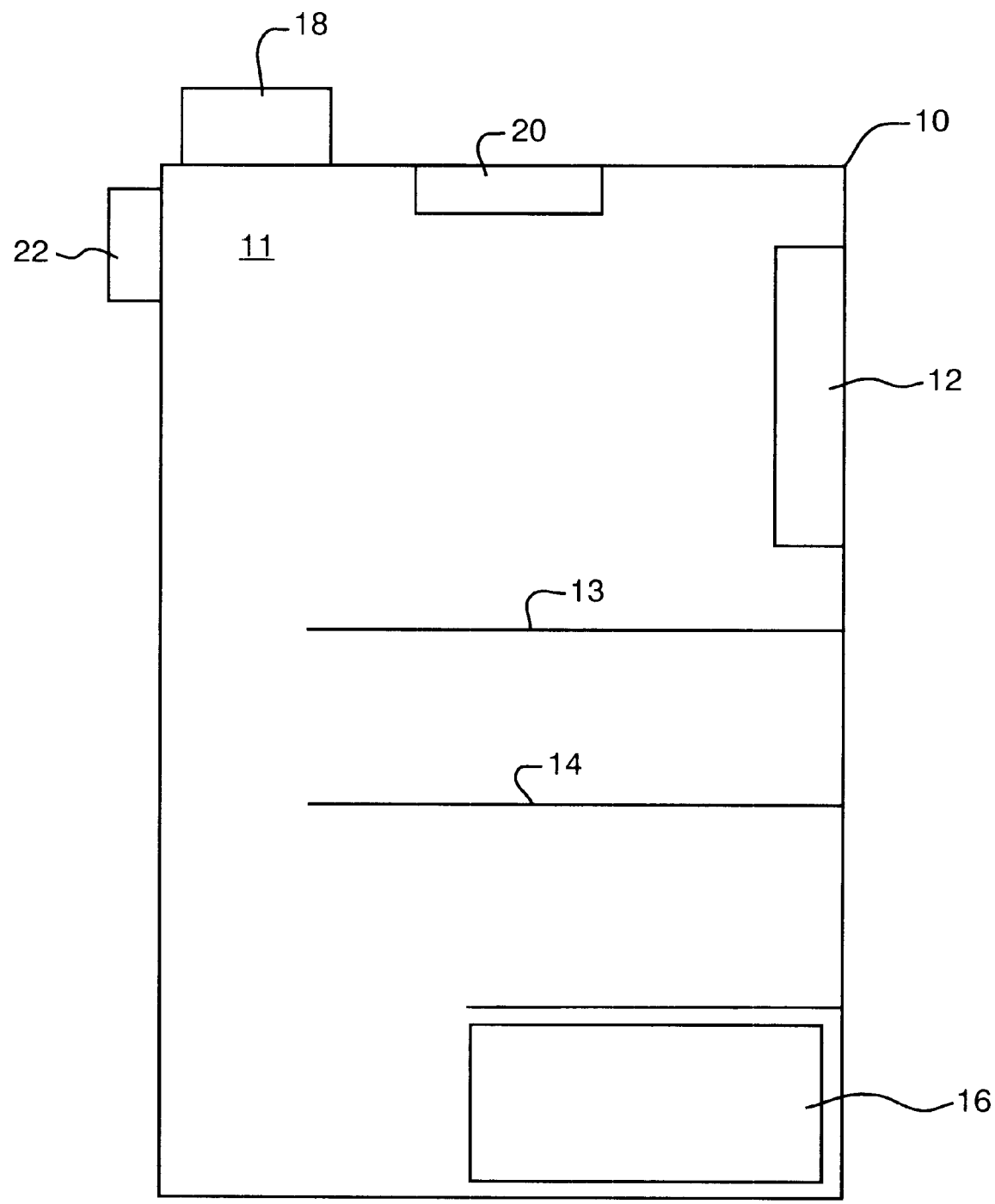

SYSTEM FOR PROLONGING USEFUL LIFE OF FOODSTUFFS IN A REFRIGERATOR

FIELD OF THE INVENTION

This invention relates to a system that uses ultraviolet light to kill bacteria in a portion or all of a refrigerator, in order to inhibit food spoilage.

BACKGROUND OF THE INVENTION

Although refrigerators by their relatively low temperature slow the bacteria-induced spoilage of food, this only delays the inevitable food spoilage problem. Typically, within a matter of days bacteria on or in the food spoils the food. And, even if the food is still edible, the presence of bacteria can lead to potential health problems.

It has been known for some time that ultraviolet light retards food spoilage. See, for example, U.S. Pat. No. 4,121,107: Apparatus for automatic low-bacteria to aseptic filling and packing of foodstuffs. However, this patent relates only to food packaging, and does not address issues concerning protection of foods once packaging has been opened, or more generally to protection of foods that are kept in a refrigerator.

SUMMARY OF THE INVENTION

The invention uses an ultraviolet light in a refrigerator to diminish the amount of organisms that may lead to spoilage of foods. When the refrigerator door is closed, an ultraviolet (UV) light is turned on, possibly only for a short, predetermined time. There could be a separate compartment in the refrigerator for this, so that only foods placed in this compartment are exposed to UV light. The light needs to be on only long enough to accomplish the killing action of UV light.

There could be up to 7 safety mechanisms for preventing inadvertent exposure of a person to the UV light.
1) the light switch on the door is used to determine positive closure of the door.
2) a time delay after door closure to increase likelihood that door is completely closed.
3) a light sensor prevents the UV light from turning on if there is not total darkness in the refrigerator, which may be if the door switch is defective or if the door is left partially open.
4) if a separate compartment is employed, it could have its own door with its own switch in addition to the main door.
5) A message regarding possible malfunction of the door interlock could be written on the inside of the refrigerator wall in a fluorescent ink which is only visible or distinguishable from the background when UV light is shining on it.
6) A short range IR movement sensor pointing towards the front of the refrigerator could be employed to extend the time delay until no one is standing in front of the refrigerator any more.
7) The UV light could be wired in parallel with a blue light which would be visible to the human eye and would alert someone to malfunction, just as propane gas is mixed with a substance that gives it the characteristic odor to alert people of gas leaks.

This invention features a system for retarding food spoilage in a refrigerator, comprising: an ultraviolet light mounted within the refrigerator; and means for turning on the light for at least a predetermined time only after the refrigerator door is shut, to bathe foodstuffs in at least a portion of the refrigerator with UV light for a sufficient time to kill at least some of the organisms on the foodstuffs.

The means for turning on the light may be responsive to the light switch on the door, so that the UV light is not turned on until positive closure of the door. The system may further include a time delay after door closure for the means for turning on, to increase the likelihood that the door is completely closed. The system may also include a light sensor to prevent the UV light from turning on if there isn't total darkness in the refrigerator, to prevent the UV light from coming on if the door switch is defective or if the door is left partially open.

The system may still further include a separate compartment in the refrigerator holding the UV light. The separate compartment may have its own door with its own switch to which the means for turning on is responsive. The system may further include a message regarding possible malfunction of the door interlock on the inside of the refrigerator wall in a fluorescent ink which is only visible or distinguishable from the background when UV light is shining on it. The system may still further include a short range IR movement sensor pointing towards the front of the refrigerator, to extend the time delay until it is more likely that no one is standing in front of the refrigerator. The UV light may be wired in parallel with a visible light, to alert to malfunction.

BRIEF DESCRIPTION OF THE DRAWING

Other objects, features and advantages will occur to those skilled in the art from the following description of the preferred embodiments, and the accompanying FIG. 1, which is a schematic diagram of a preferred embodiment of the system of this invention.

DESCRIPTION OF THE PREFERRED EMBODIMENTS

The invention uses an ultraviolet light in a refrigerator to diminish the amount of organisms that may lead to spoilage of foods. When the refrigerator door is closed, the UV light is turned on, possibly only for a short, predetermined time. There could be a separate compartment in the refrigerator for this, so that only foods placed in this compartment are exposed to UV light. The light needs to be on only long enough to accomplish the killing action of UV light.

There is shown in FIG. 1 refrigerator 10 modified according to this invention. UV light and light controller and visible light sensor 12 is placed inside of refrigerator 10 to irradiate the whole of, or a desired portion of, the inside 11 of the refrigerator, having shelves 13 and 14. Compartment 16, either closed by a door or comprising a sliding drawer as is the case with meat and vegetable drawers, may be used as a UV compartment, in which case item 12 is inside of enclosure 16. The door or drawer may then have its own switch that turns on the UV light only when the door or drawer is closed.

Refrigerator 20 has standard interior visible light 20, controlled by a door light switch, also standard on refrigerators. The UV light may also be enabled by this switch, to decrease the possibility of the UV light coming on while the refrigerator door is open. Also, a time delay built into the controller could be used to increase the likelihood that the door is fully closed before the UV light is turned on. The light sensor can be used to disable the UV light if visible light is sensed. Preferably, the UV light is turned on by the controller in item 12 only for an appropriate time period (to properly irradiate the food) after each time the refrigerator door is closed.

A message regarding possible malfunction of the door interlock could be written on the inside of the refrigerator wall in a fluorescent ink which is only visible or distinguishable from the background when UV light is shining on it. Also, a short range IR movement sensor 22 pointing towards the front of the refrigerator could be employed to extend the UV light turn on time delay until no one is standing in front of the refrigerator. The UV light could be wired in parallel with external visible light 18, which would be visible to the human eye and would be turned on if the door was open and the UV light was on, to alert someone to malfunction.

In addition, to prevent certain classes of foods from being potentially damaged by UV light, the manufacturers of those foods could be advised to apply labels to the packaging indicating either that the given food would benefit or not benefit from being in the UV drawer.

Other embodiments will occur to those skilled in the art and are within the following claims.

What is claimed is:

1. A system for retarding food spoilage in a refrigerator, comprising:

an ultraviolet light mounted within the refrigerator;

means for turning on the light for at least a predetermined time only after the refrigerator door is shut, to bathe foodstuffs in at least a portion of the refrigerator with UV light for a sufficient time to kill at least some of the organisms on the foodstuffs; and a light sensor in the refrigerator to prevent the UV light from turning on if there is not total darkness in the refrigerator, to prevent the UV light from coming on if the door switch is defective or if the door is left partially open.

2. The system of claim 1 wherein the means for turning on the light is responsive to the light switch on the door, so that the UV light is not turned on until positive closure of the door.

3. The system of claim 1 further including a time delay after door closure for the means for turning on, to increase the likelihood that the door is completely closed.

4. The system of claim 1 further including a light sensor in the refrigerator to prevent the UV light from turning on if there is not total darkness in the refrigerator, to prevent the UV light from coming on if the door switch is defective or if the door is left partially open.

5. The system of claim 1 further including a separate compartment in the refrigerator holding the UV light.

6. The system of claim 5 wherein the separate compartment has its own door with its own switch to which the means for turning on is responsive.

7. The system of claim 1 further including a message regarding possible malfunction of the door interlock on the inside of the refrigerator wall in a fluorescent ink which is only visible or distinguishable from the background when UV light is shining on it.

8. The system of claim 1 further including a short range IR movement sensor pointing towards the front of the refrigerator, to extend the time delay until it is more likely that no one is standing in front of the refrigerator.

9. A system for retarding food spoilage in a refrigerator, comprising:

an ultraviolet light mounted within the refrigerator;

means for turning on the light for at least a predetermined time only after the refrigerator door is shut, to bathe foodstuffs in at least a portion of the refrigerator with UV light for a sufficient time to kill at least some of the organisms on the foodstuffs; and a message regarding possible malfunction of the door interlock on the inside of the refrigerator wall in a fluorescent ink which is only visible or distinguishable from the background when the UV light is shining on it.

10. The system of claim 9 wherein the means for turning on the light is responsive to the light switch on the door, so that the UV light is not turned on until positive closure of the door.

11. The system of claim 9 further including a time delay after door closure for the means for turning on, to increase the likelihood that the door is completely closed.

12. The system of claim 9 further including a separate compartment in the refrigerator holding the UV light.

13. The system of claim 12 wherein the separate compartment has its own door with its own switch to which the means for turning on is responsive.

14. The system of claim 11 further including a short range IR movement sensor pointing towards the front of the refrigerator, to extend the time delay until it is more likely that no one is standing in front of the refrigerator.

15. The system of claim 9 wherein the UV light is wired in parallel with a visible light, to alert to malfunction.

16. A system for retarding food spoilage in a refrigerator, comprising:

an ultraviolet light mounted within the refrigerator;

means for turning on the light for at least a predetermined time only after the refrigerator door is shut, to bathe foodstuffs in at least a portion of the refrigerator with UV light for a sufficient time to kill at least some of the organisms on the foodstuffs;

a time delay after door closure for the means for turning on, to increase the likelihood that the door is completely closed; and a short range IR movement sensor pointing towards the front of the refrigerator, to extend the time delay until it is more likely that no one is standing in front of the refrigerator.

17. The system of claim 16 wherein the means for turning on the light is responsive to the light switch on the door, so that the UV light is not turned on until positive closure of the door.

18. The system of claim 16 further including a light sensor in the refrigerator to prevent the UV light from turning on if there is not total darkness in the refrigerator, to prevent the UV light from coming on if the door switch is defective or if the door is left partially open.

19. The system of claim 16 further including a separate compartment in the refrigerator holding the UV light.

20. The system of claim 19 wherein the separate compartment has its own door with its own switch to which the means for turning on is responsive.

21. The system of claim 16 wherein the UV light is wired in parallel with a visible light, to alert to malfunction.

* * * * *